(12) United States Patent
Merce Vidal et al.

(10) Patent No.: US 8,097,643 B2
(45) Date of Patent: *Jan. 17, 2012

(54) INDOL-4 SULFONAMIDE DERIVATIVES, THEIR PREPARATION AND THEIR USE 5-HT-6 AS MODULATORS

(75) Inventors: Ramon Merce Vidal, Barcelona (ES); Xavier Codony Soler, Mataro (ES); Alberto Dordal Zueras, Barcelona (ES)

(73) Assignee: Laboratorios del Dr. Esteve S. A., Barcelona (ES)

( * ) Notice: Subject to any disclaimer, the term of this patent is extended or adjusted under 35 U.S.C. 154(b) by 484 days.

This patent is subject to a terminal disclaimer.

(21) Appl. No.: 10/566,164

(22) PCT Filed: Jul. 29, 2004

(86) PCT No.: PCT/EP2004/008512
§ 371 (c)(1),
(2), (4) Date: Jan. 16, 2007

(87) PCT Pub. No.: WO2005/013978
PCT Pub. Date: Feb. 17, 2005

(65) Prior Publication Data
US 2007/0185158 A1 Aug. 9, 2007

(30) Foreign Application Priority Data
Jul. 30, 2003 (ES) .................................. 200301807

(51) Int. Cl.
*A61K 31/404* (2006.01)
*C07D 209/10* (2006.01)
(52) U.S. Cl. .................................. 514/415; 548/503
(58) Field of Classification Search ............ 548/503
See application file for complete search history.

(56) References Cited

U.S. PATENT DOCUMENTS

| | | | |
|---|---|---|---|
| 6,521,658 B1 * | 2/2003 | Li et al. ............ | 514/415 |
| 2003/0191124 A1 | 10/2003 | Merce-Vidal et al. | |
| 2005/0032791 A1 | 2/2005 | Merc-Vidal et al. | |
| 2005/0065202 A1 | 3/2005 | Vidal et al. | |

FOREIGN PATENT DOCUMENTS

| | | |
|---|---|---|
| EP | 0 733 628 A1 | 9/1996 |
| EP | 0815861 | 1/1998 |
| ES | 2 121 223 | 11/1998 |
| WO | 00/46195 | 8/2000 |
| WO | 00/46915 | 8/2000 |
| WO | WO 01/32646 A2 | 5/2001 |
| WO | 02/060871 | 8/2002 |
| WO | 03/042175 | 5/2003 |

OTHER PUBLICATIONS

RN 148773-85-7, retrieved from CAPLUS on Feb. 26, 2009.*
Vippagunta, et al. Advanced Drug Delivery Reviews 48 (2001) 3-26.*
FDA mulls drug to slow late-stage Alzheimer's [online],[retrieved on Sep. 23, 2003].Retrieved from the Internet, URL; http://www.cnn.com120031HEALTHIconditions/O91241alzheimers.drug.ap/indexhtml>.*
Cecil Textbook of Medicine, 20th edition (1996), vol. 2, pp. 1992-1996.*
Cecil Textbook of Medicine, 20th edition (1996), vol. 2, pp. 2050-2057.*
U.S. Appl. No. 10/566,094, filed Jan. 27, 2006, Merce Vidal, et al.
U.S. Appl. No. 10/566,403, filed Jan. 30, 2006, Merce Vidal, et al.
U.S. Appl. No. 10/566,101, filed Jan. 27, 2006, Merce Vidal, et al.
U.S. Appl. No. 10/566,100, filed Jan. 27, 2006, Torrens Jover, et al.
U.S. Appl. No. 10/566,402, filed Jan. 30, 2006, Torrens Jover, et al.
U.S. Appl. No. 11/679,344, filed Feb. 27, 2007, Merce Vidal.
U.S. Appl. No. 11/673,328, filed Feb. 9, 2007, Merce Vidal, et al.
Hoyer, D., et al., "5-HT Receptor Classification and Nomenclature: Towards a Harmonization with the Human Genome", Review, Neuropharmacology, vol. 36. No. 4/5, 1997, pp. 419-428. Monsma, J. Frederick, Jr. et al., "Cloning and Expression of a Novel Serotonin Receptor with High Affinity for Trycyclic Psychotropic Drugs", Accelerated Communication, Molecular Pharmacology, 43, pp. 320-327, 1992.
Ruat, Martial, et al., "A novel rat serotonin (5-HT$_6$) receptor: molecular cloning, localization and stimulation of camp accumulation", Biochemical and Biophysical Research Communications, vol. 193. No. 1, 1993, May 28, 1993, pp. 268-276.
Kohen, Ruth, et al., "Cloning, Characterization, and Chromosomal Localization of a Human 5-HT$_6$ Serotonin Receptor", Journal of Neurochemistry, vol. 66, No. 1, 1996, pp. 47-56.
Yoshioka, M., et al., "Central Distribution and Function of 5-HT$_6$ Receptor Subtype in the Rat Brain", First Department of Pharmacology, Hokkaido University School of Medicine, Kita-15, Nishi-7, Kita-ku Sapporo 060, Japan, 1998. 861, 244.

(Continued)

*Primary Examiner* — Shawquia Young
(74) *Attorney, Agent, or Firm* — Oblon, Spivak, McClelland, Maier & Neustadt, L.L.P.

(57) ABSTRACT

The present invention refers to new sulfonamide derivatives, of general formula (1a, 1b, 1c), optionally in form of one of their stereoisomers, preferably enantiomers or diastereomers, their racemate, or in form of a mixture of at least two of their stereoisomers, preferably enantiomers or diastereomers, in any mixing ratio, or their salt thereof s, preferably the corresponding, physiologically acceptable salt thereofs, or corresponding solvate thereofs; to the processes for their preparation, to their application as medicaments in human and/or veterinary therapeutics, and to the pharmaceutical compositions containing them.

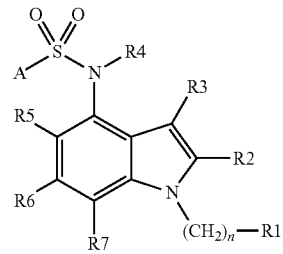

(Ia, Ib, Ic)

18 Claims, No Drawings

OTHER PUBLICATIONS

Turnbull, V. Andrew, et al., "Selective Antagonism of the NPY Y5 Receptor Does Not Have a Major Effect on Feeding in rats", Diabetes, vol. 51, Aug. 2002, pp. 2441-2449.

Bourson, Anne, et al., "Involvement of 5-$HT_6$ receptors in nigrostriatal function in rodents", British Journal of Pharmacology (1998) 125, pp. 1562-1566.

Rogers, D.C., et al., "Cognitive enhancement effects of the selective 5-$HT_6$ antagonist SB-271046", Br. J. Pharmacol. Suppl., 1999, 127, 22p.

Bourson, Anne, et al., "Determination of the Role of the 5-$HT_6$ Receptor in the Rat Brain: A Study using Antisense Oligonucleotides [1]", Pharamcol, Exp. Ther..1995, 274, pp. 173-180.

Sleight, A.J., et al., "Effects of altered 5-$HT_6$ expression in the rat: functional studies using antisense oligonucleotides", Behavioral Brain Research 73 (1996), pp. 245-248.

Branchek, A. Theresa, et al., "5$HT_6$ Receptors as Emerging Targets for Drug Discovery", Annu. Rev. Pharmacol. Toxicol, 2000, 40,pp. 319-334.

Routledge, Carol, et al., "Characterization of SB-271046: a potent, selective and orally active 5-$HT_6$ receptor antagonist", British Journal of Pharmacology (2000) vol. 130, pp. 1606-1612.

Roth, L. Bryan, et al., "Binding of Typical and Atypical Antipsychotic Agents to 5-Hydroxytryptamine-6 and 5-Hydroxytryptamine-7 Receptors", The Journal of Pharmacology and Experimental Therapeutics. vol. 268, No. 3, pp. 1403-1410, (1994).

Glatt, E. Charles, et al., "Clozapine: Selective Labeling of Sites Resembling 5-$HT_6$ Serotonin Receptors May Reflect Psychoactive Profile", Molecular Medicine, vol. 1. No. 4, May 1995 pp. 398-406.

Shinkai, Takahiro, et al., "Association Study of the 5-$HT_6$ Receptor Gene in Schizophrenia", American Journal of Medical Genetics (Neuropsychiatric Genetics) 88, pp. 120-122 (1999).

Gerard, Caroline, et al., "Immuno-localization of serotonin 5$HT_6$ receptor-like material in the rat central nervous system", Brain Research 746 (1997) pp. 207-219.

Pranzatelli, R. Michael, "Serotonergic drugs and movement disorders in humans", Drugs of Today vol. 33, No. 6, 1997, pp. 379-392.

Gilbert, E.E., "Recent developments in preparative sulfonation and sulfation", SYNTHESIS, International Journal of Methods in Synthetic Organic Chemistry No. 1: Sep. 1969.

Munson, P., et al., "LIGAND: a versatile computerized approach for characterization of ligand-binding systems", Analytical Biochemistry, 1980, 107, pp. 220-239.

Kask, Ants, et al., "Neuropeptide Y $Y_5$ receptor antagonist CGP71683A: the effects on food intake and anxiety-related behavior in the rat", European Journal of Pharmacology 414, 2001, pp. 215-224.

Churchill, et al., "Pharmaceutics: The Science of Dosage Forms" Second Edition, 2002.

Swarbrick, et al., Encyclopedia of Pharmaceutical Technology, second edition, 2002.

Gilbert, S. Banker and Christopher t. Rhodes, "Modem Pharmaceutics", Fouth Edition, vol. 121, Drugs and the Pharmaceutical Sciences, 2002.

Lachman, et al., "The Theory and Practeice of Industrial Pharmacy", Thrid Edition, 1986.

Rathbone, et al., "Modified-Release Drug Delivery Technology", Drugs and the Pharmaceutical Sciences, vol. 126, 2002.

Bruck, D. Stephen, Ph.D., "Controlled Drug Delivery" Basic Concepts, vol. 1, 1983.

Mathiowitz, E. (Ed.) John Wiley & Sons, Inc. New York, "Oral drug delivery, small intestine and colon", Encyclopedia of Controlled Drug Delivery, 1999, vol. 2. pp. 698-728.

Warren D. Hirst, et al.; "Characterization of [$^{125}$I]-SB-258585 Binding to Human Recombinant and Native 5-HT6 Receptors in Rat, Pig and Human Brain Tissue", British Journal of Pharmacology (2000) 130, pp. 1597-1605.

M.L. Woolley, et al. "A Role for 5-$ht_6$ Receptors in Retention of Spatial Learning in the Morris Water Maze", Neuropharmacology 41 (2001), pp. 210-219.

Magid Abou-Gharbia, et al. "Synthesis and Anti-Arrhythmic Activity of Cycloalkaneindoles", J. Med Chem. 23, (1988), pp. 373-377.

J. F. W. McOmie, et al., "Protective Groups in Organic Chemistry", Plenum Press. London, and New York. 1973.

Theodora W. Greene, et al., "Protective Groups in Organic Synthesis", Second Edition, A Wiley-Interscience Publication John Wiley & Sons, Inc., New York/ Chichester/ Brisbane/ Toronto/ Singapore.

Oral Drug Delivery, Traditional, Supplied by the British Library- "The world's knowledge".

* cited by examiner

INDOL-4 SULFONAMIDE DERIVATIVES, THEIR PREPARATION AND THEIR USE 5-HT-6 AS MODULATORS

The present invention refers to new sulfonamide derivatives, of general formula (Ia, Ib, Ic),

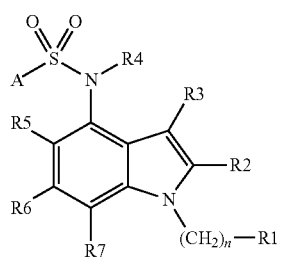

(Ia, Ib, Ic)

optionally in form of one of their stereoisomers, preferably enantiomers or diastereomers, their racemate, or in form of a mixture of at least two of their stereoisomers, preferably enantiomers or diastereomers, in any mixing ratio, or their salts, preferably the corresponding, physiologically acceptable salts, or corresponding solvates; to the processes for their preparation, to their application as medicaments in human and/or veterinary therapeutics, and to the pharmaceutical compositions containing them.

The new compounds of the present invention may be used in the pharmaceutical industry as intermediates and for preparing medicaments.

The superfamily of serotonin receptors (5-HT) comprises 7 classes ($5\text{-HT}_1\text{-}5\text{-HT}_7$), which cover 14 human subclasses [D. Hoyer, et al., *Neuropharmacology*, 1997, 36, 419]. The $5\text{-HT}_6$ receptor has been the last serotonin receptor identified by molecular cloning in rats [F. J. Monsma, et al., *Mol. Pharmacol.*, 1993, 43, 320; M. Ruat, et al., *Biochem. Biophys. Res. Commun.*, 1993, 193, 268] as well as in humans [R. Kohen, et al., *J. Neurochem.*, 1996, 66, 47]. The compounds with an affinity for the $5\text{-HT}_6$ receptor are useful in treating different disorders of the Central Nervous System and of the Gastrointestinal system, as well as the irritable bowel syndrome. The compounds with an affinity for the $5\text{-HT}_6$ receptor are useful for treating anxiety, depression and cognitive memory disorders [M. Yoshioka, et al., *Ann. NY Acad. Sci.*, 1998, 861, 244; A. Bourson, et al., *Br. J. Pharmacol.*, 1998, 125, 1562; D. C. Rogers, et al., *Br. J. Pharmacol. Suppl.*, 1999, 127, 22P; A. Bourson, et al., *J. Pharmacol. Exp. Ther.*, 1995, 274, 173; A. J. Sleight, et al., *Behav. Brain Res.*, 1996, 73, 245; T. A. Branchek, et al., *Annu. Rev. Pharmacol. Toxicol.*, 2000, 40, 319; C. Routledge, et al., *Br. J. Pharmacol.*, 2000, 130, 1606]. It has been shown that the typical and atypical antipsychotics for treating schizophrenia have a high affinity for the $5\text{-HT}_6$ receptors [B. L. Roth, et al., *J. Pharmacol. Exp. Ther.*, 1994, 268, 1403; C. E. Glatt, et al., *Mol. Med.*, 1995, 1, 398; F. J. Mosma, et al., *Mol. Pharmacol.*, 1993, 43, 320; T. Shinkai, et al, *Am. J. Med. Genet.*, 1999, 88, 120]. The compounds with an affinity for the $5\text{-HT}_6$ receptor are useful for treating infantile hyperkinesia (ADHD, attention deficit/hyperactivity disorder) [V. D. Hirst, et al., *Br. J. Pharmacol.*, 2000, 130, 1597; C. Gérard, et al., *Brain Research*, 1997, 746, 207; M. R. Pranzatelli, *Drugs of Today*, 1997, 33, 379].

Patent application WO 01/32646 discloses sulfonamides derived from bicycles, whereby each of the rings is 6-membered, aromatic or heteroaromatic rings with $5\text{-HFT}_6$ receptor antagonist activity.

Patent application EP 0 733 628 discloses sulfonamides derived from indole with $5\text{-HT}_{1F}$ receptor antagonist activity, useful for the treatment of migraines.

Furthermore, it has been shown that the $5\text{-HT}_6$ receptor also plays a role in the ingestion of food [*Neuropharmacology*, 41, 2001, 210-219].

Eating disorders, particularly obesity, are a serious and increasingly frequent threat for the health of humans from all age groups, since they increase the risk of developing other serious and even mortal diseases, preferably diabetes and coronary artery diseases.

Therefore, an object of the present invention was to provide new compounds, particularly suitable as active substances in medicaments, preferably in medicaments for $5\text{-HT}_6$ receptor regulation, for cognitive enhancement, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, preferably Alzheimer's disease, Parkinson's disease, Huntington's disease and Multiple Sclerosis, schizophrenia, psychosis or infantile hyperkinesia (ADHD, attention deficit/hyperactivity disorder), and other disorders mediated by the $5\text{-HT}_6$ serotonin receptor in humans and/or in animals, preferably in mammals, more preferably in humans.

It has been found that the indol-4-yl sulfonamide compounds of general formulas (Ia, Ib, Ic) described below show an affinity for the $5\text{-HT}_6$ receptor.

These compounds are therefore suitable for preparing a medicament for preventing and/or treating disorders related related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, preferably Alzheimer's disease, Parkinson's disease, Huntington's disease and Multiple Sclerosis, schizophrenia, psychosis or infantile hyperkinesia (ADHD, attention deficit/hyperactivity disorder), and other disorders mediated by the $5\text{-HT}_6$ serotonin receptor in mammals, including man. These compounds are also suitable for the preparation of a medicament for cognitive enhancement.

Thus, one aspect of the present invention are compounds of general formula (Ia),

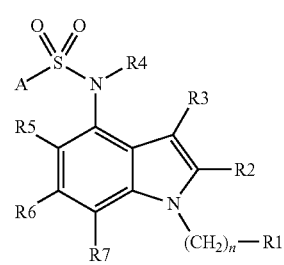

(Ia)

wherein
R$^1$ represents a —NR$^8$R$^9$ radical or a saturated or unsaturated, optionally at least mono-substituted cycloaliphatic radical, which may contain at least one heteroatom as a ring member and/or which may be condensed with a saturated or unsaturated, optionally at least mono-substituted, optionally at least one heteroatom as a ring member containing mono- or bicyclic cycloaliphatic ring system, R$^2$, R$^3$, R$^5$, R$^6$ and R$^7$, identical or different, each represent hydrogen, halogen, nitro, alkoxy, cyano, a saturated or unsaturated, linear or branched, optionally at least mono-substituted aliphatic radical, or an optionally at least mono-substituted phenyl or heteroaryl radical, R$^4$ is hydrogen or a saturated or unsaturated, linear or branched, optionally at least mono-substituted aliphatic radical, R$^8$ and R$^9$, identical or different, each represent hydrogen or a saturated or unsaturated, linear or branched, optionally at least mono-substituted aliphatic radical, with the proviso that R$^8$ and R$^9$ are not hydrogen at the same time, and if one of them, R$^8$ or R$^9$, is a saturated or unsaturated, linear or branched, optionally at least mono-substituted C$_1$-C$_4$ aliphatic radical, the other one is a saturated or unsaturated, linear or branched, optionally at least mono-substituted aliphatic radical with at least five carbon atoms, or R$^8$ and R$^9$ together with bridging nitrogen atom form a saturated or unsaturated, optionally at least mono-substituted heterocyclic ring, which may contain at least one additional heteroatom as a ring member and/or may be condensed with a saturated or unsaturated, optionally at least mono-substituted mono- or bicyclic cycloaliphatic ring system, which may optionally contain at least one heteroatom as a ring member, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, and
n is 0, 1, 2, 3 or 4;
optionally in form of one of its stereoisomers, preferably enantiomers or diastereomers, its racemate or in form of a mixture of at least two of its stereoisomers, preferably enantiomers or diastereomers, in any mixing ratio, or a salt thereof, preferably a corresponding, physiologically acceptable salt thereof, or a corresponding solvate thereof.

Another aspect of the present invention are compounds of general formula (Ib)

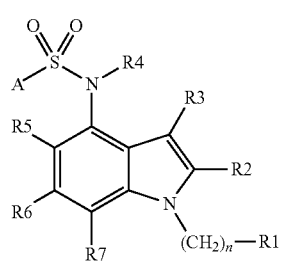

(Ib)

wherein
R$^1$ represents a —NR$^8$R$^9$ radical,
R$^2$, R$^3$, R$^5$, R$_6$ and R$^7$, identical or different, each represent hydrogen, halogen, nitro, alkoxy, cyano, a saturated or unsaturated, linear or branched, optionally at least mono-substituted aliphatic radical, or an optionally at least mono-substituted phenyl or an optionally at least mono-substituted heteroaryl radical, R$^4$ is hydrogen or a saturated or unsaturated, linear or branched, optionally at least mono-substituted aliphatic radical, R$^8$ and R$^9$, identical or different, each represent hydrogen or a saturated or unsaturated, linear or branched, optionally at least mono-substituted C$_{1-4}$ aliphatic radical, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, and
n is 0, 1, 2, 3 or 4;
optionally in form of one of its stereoisomers, preferably enantiomers or diastereomers, its racemate or in form of a mixture of at least two of its stereoisomers, preferably enantiomers or diastereomers, in any mixing ratio, or a salt thereof, preferably a corresponding, physiologically acceptable salt thereof, or a corresponding solvate thereof.

Yet another aspect of the present invention are compounds of general formula (Ic),

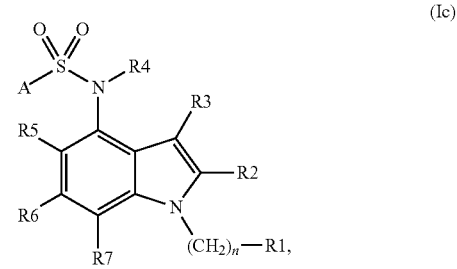

(Ic)

wherein
R$^1$ represents a —NR$^8$R$^9$ radical or a saturated or unsaturated, optionally at least mono-substituted cycloaliphatic radical, which may contain at least one heteroatom as a ring member and/or which may be condensed with a saturated or unsaturated, optionally at least mono-substituted, optionally at least one heteroatom as a ring member containing mono- or bicyclic cycloaliphatic ring system, R$^2$, R$^3$, R$^5$, R$^6$ and R$^7$, identical or different, each represent hydrogen, halogen, nitro, alkoxy, cyano, a saturated or unsaturated, linear or branched, optionally at least mono-substituted aliphatic radical, or an optionally at least mono-substituted phenyl or an optionally at least mono-substituted heteroaryl radical, R$^4$ represents hydrogen or a saturated or unsaturated, linear or branched, optionally at least mono-substituted aliphatic radical, R$^8$ and R$^9$, identical or different, each represent hydrogen or a saturated or unsaturated, linear or branched, optionally at least mono-substituted aliphatic radical, or
R$^8$ and R$^9$ together with bridging nitrogen atom form a saturated or unsaturated, optionally at least mono-substituted heterocyclic ring, which may contain at least one additional heteroatom as a ring member and/or may be condensed with a saturated or unsaturated, optionally at least mono-substituted mono- or bicyclic cycloaliphatic ring system, which may optionally contain at least one heteroatom as a ring member, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, and n is 0, 1, 2, 3 or 4;

optionally in form of one of its stereoisomers, preferably enantiomers or diastereomers, its racemate or in form of a mixture of at least two of its stereoisomers, preferably enantiomers or diastereomers, in any mixing ratio, or a salt thereof, preferably a corresponding, physiologically acceptable salt thereof, or a corresponding solvate thereof.

If one or more of the moieties $R^2$-$R^9$ represent a saturated or unsaturated aliphatic radical, that is, an alkyl, alkenyl or alkynyl radical which is substituted by one or more substituents, each one of these substituents may preferably be chosen, unless otherwise defined, from the group consisting of hydroxy, fluorine, chlorine, bromine and trifluoromethyl.

If $R^1$ is a saturated or unsaturated, optionally at least one heteroatom as a ring member containing cycloaliphatic radical, which is substituted by one or more substituents and/or is condensed with a saturated or unsaturated, optionally at least one heteroatom as a ring member containing mono- or bicyclic cycloaliphatic ring system, which is substituted by one or more substituents, each one of these substituents may preferably be chosen, unless otherwise defined, from the group consisting of hydroxy, fluorine, chlorine, bromine, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, preferably from the group consisting of linear or branched $C_1$-$C_6$ alkyl and benzyl.

The heteroatoms of said cycloaliphatic radical and/or of said mono- or bicyclic cycloaliphatic ring may, independently from one another, preferably be chosen from the group consisting of nitrogen, sulphur and oxygen, more preferably nitrogen is chosen as a heteroatom.

Said cycloaliphatic radical may contain 0, 1, 2 or 3 heteroatoms chosen from the above mentioned group, preferably it contains 0, 1 or 2 heteroatoms chosen from the above mentioned group.

If $R^8$ and $R^9$ together with the bridging nitrogen atom form a saturated or unsaturated, optionally at least mono-substituted heterocyclic ring, which may contain at least one further heteroatom as a ring member and/or which is condensed with a saturated or unsaturated mono- or bicyclic cycloaliphatic ring system, which may contain at least one heteroatom as a ring member and/or which is substituted by one or more substituents, each one of these substituents may preferably be chosen, unless otherwise defined, from the group consisting of hydroxy, fluorine, chlorine, bromine, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, preferably from the group consisting of linear or branched $C_1$-$C_6$ alkyl and benzyl.

If the heterocyclic ring contains one or more additional heteroatoms, and/or if one or both rings of the mono- or bicyclic ring system contain one or more heteroatoms, these heteroatoms may, independently from one another, preferably be chosen from the group consisting of nitrogen, sulphur and oxygen, more preferably nitrogen is chosen as a heteroatom.

Said heterocyclic ring may contain 0, 1, 2 or 3 additional heteroatoms chosen from the above mentioned group, preferably it contains 0 or 1 heteroatoms chosen from the above mentioned group.

If A is a mono- or polycyclic aromatic ring system which may be bonded via an alkylene, alkenylene or alkynylene group and/or which may contain at least one heteroatom as a ring member and/or which may be substituted by one or more substituents, each one of these substituents may preferably be chosen from the group consisting of hydroxy, halogen, linear or branched $C_1$-$C_6$ alkyl, linear or branched $C_1$-$C_6$ alkoxy, —O-phenyl, linear or branched $C_1$-$C_6$ perfluoroalkyl, linear or branched $C_1$-$C_6$ perfluoroalkoxy, an optionally at least mono-substituted phenyl radical and 5- or 6-membered heteroaryl, more preferably from the group consisting of halogen, linear or branched $C_1$-$C_6$ alkyl, —O-phenyl, an optionally at least mono-substituted phenyl radical and 5- or 6-membered heteroaryl, even more preferably from the group consisting of fluorine, chlorine, —O-phenyl, linear or branched $C_1$-$C_6$ alkyl, an optionally at least mono-substituted phenyl radical and 5- or 6-membered heteroaryl.

If one or more of the rings of the mono- or polycyclic aromatic ring system contain one or more heteroatoms, these heteroatoms—like the heteroatoms of a previously mentioned 5- or 6-membered heteroaryl radical—may preferably be chosen from the group consisting of nitrogen, sulphur and oxygen.

If the previously mentioned phenyl radical is itself substituted by one or more substituents, each one of these substituents may preferably be chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, trifluoromethyl radical, cyano radical and a —$NR^{12}R^{13}$ radical, wherein $R^{12}$ and $R^3$, identical or different, represent hydrogen or a linear or branched $C_1$-$C_6$ alkyl.

If the previously mentioned alkylene, alkenylene or alkynylene group is substituted by one or more substituents, each of these substituents may preferably be chosen from the group consisting of hydroxy, halogen, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy or an optionally at least mono-substituted phenyl radical.

If said phenyl radical is itself substituted by one or more substituents, each one of these substituents may preferably be chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, trifluoromethyl radical, cyano radical and a —$NR^{12}R^{13}$ radical, wherein $R^{12}$ and $R^{13}$, identical or different, represent hydrogen or a linear or branched $C_1$-$C_6$ alkyl.

If one or more of the substituents $R^2$, $R_3$, $R_5$, $R_6$ and $R^7$ represents an alcoxy radical, said radical may have 1 to 6, preferably 1 to 3 carbon atoms.

Those skilled in the art understand that the term "condensed" indicates that the condensed rings share more than one atom. The terms "annulated" or "fused" may also be used for this type of bonding.

Sulfonamide derivatives of general formula (Ia) are preferred, wherein $R^1$ represents a —$NR^8R^9$ radical or a saturated or unsaturated optionally at least mono-substituted 5- or 6-membered cycloaliphatic radical, which may optionally contain at least one heteroatom as a ring member and which may be condensed with a saturated or unsaturated, optionally at least mono-substituted mono- or bicyclic cycloaliphatic ring, which may optionally contain at least one heteroatom as a ring member, whereby the rings of the ring system are 5- or 6-membered, more preferably $R^1$ represents a —$NR^8R^9$ radical or a radical chosen from the group consisting of

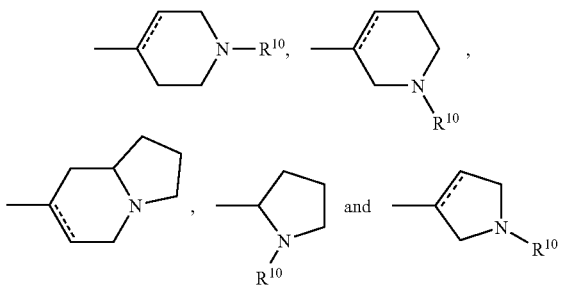

wherein, if present, the dotted line represents an optional chemical bond, and $R^{10}$ represents hydrogen, a linear or branched $C_1$-$C_6$ alkyl radical or a benzyl radical, preferably hydrogen or a $C_1$-$C_2$ alkyl radical and $R^2$-$R^9$, A and n are defined as above.

Sulfonamide derivatives of general formula (Ia) are also preferred, wherein $R^2$, $R^3$, $R^5$, $R^6$ and $R^7$, identical or dfferent, each represent hydrogen, a linear or branched, optionally at least mono-substituted $C_1$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical, more preferably $R^2$, $R^3$, $R^5$, $R^6$ and $R^7$, identical or different, each represent hydrogen or a linear or branched, optionally at least mono-substituted $C_1$-$C_6$ alkyl radical, even more preferably $R^2$, $R^3$, $R^5$, $R^6$ and $R^7$ each represent hydrogen or a $C_1$-$C_2$ alkyl radical and $R^1$, $R^4$, $R^8$, $R^9$, A and n are defined as above.

Sulfonamide derivatives of general formula (Ia) are also preferred, wherein $R^4$ represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical more preferably $R^4$ represents hydrogen or a linear or branched, optionally at least mono-substituted $C_1$-$C_6$ alkyl radical, even more preferably $R^4$ represents hydrogen or a $C_1$-$C_2$ alkyl radical and $R^1$-$R^3$, $R^5$-$R^9$, A and n are defined as above.

Furthermore, sulfonamide derivatives of general formula (Ia) are also preferred, wherein $R^3$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical, a linear or branched, optionally at least mono-substituted $C_2$-$C_{10}$ alkynyl radical, with the proviso that $R^8$ and $R^9$ do not represent hydrogen at the same time, and if one of them, $R^8$ and $R^9$, represents a saturated or unsaturated, linear or branched, optionally at least mono-substituted $C_1$-$C_4$ aliphatic radical, the other one represents a saturated or unsaturated, linear or branched, optionally at least mono-substituted, aliphatic radical with at least five carbon atoms, or $R^8$ and $R^9$ together with bridging nitrogen atom form a saturated or unsaturated, optionally at least mono-substituted 5- or 6-membered heterocyclic ring which may contain at least one additional heteroatom as a ring member and/or which may be condensed with a saturated or unsaturated, optionally at least mono-substituted mono- or bicyclic cycloaliphatic ring, which may optionally contain at least one heteroatom as a ring member, whereby the rings of the ring system are 5- 6- or 7-membered and $R^1$-$R^7$, A and n are defined as above.

Particularly preferred are sulfonamide derivatives of general formula (Ia), wherein $R^8$ and $R^9$, identical or different, each represent hydrogen or a linear or branched $C_1$-$C_{10}$ alkyl radical, with the proviso that $R^8$ and $R^9$ do not represent hydrogen at the same time, and if one of them, $R^8$ and $R^9$, represents a saturated or unsaturated, linear or branched, optionally at least mono-substituted $C_1$-$C_4$ aliphatic radical, the other one represents a saturated or unsaturated, linear or branched, optionally at least mono-substituted, aliphatic radical with at least five carbon atoms, or $R_8$ and $R^9$ together with bridging nitrogen atom form a radical chosen from the group consisting of

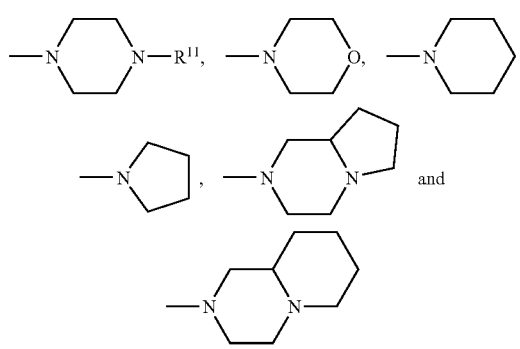

wherein $R^{11}$, if present, represents hydrogen, a linear or branched $C_1$-$C_6$ alkyl radical or a benzyl radical, preferably hydrogen, or a $C_1$-$C_2$ alkyl radical, and $R^1$-$R^9$, A and n are defined as above.

Furthermore, sulfonamide derivatives of general formula (Ia) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

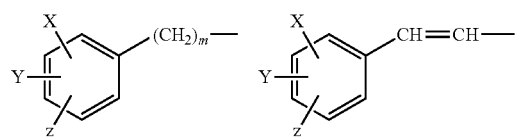

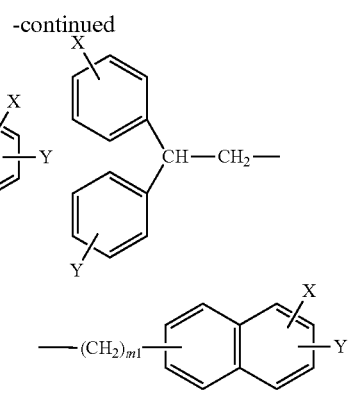
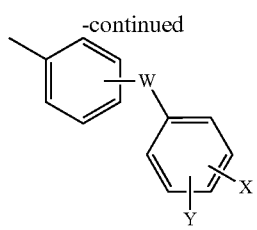

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore, sulfonamide derivatives of general formula (Ia) are preferred, wherein A represents an optionally at least mono-substituted mono- or polycyclic aromatic ring system, wherein the ring(s) is/are 5 or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group, and/or wherein the ring(s) may contain at least one heteroatom as a ring member, more preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

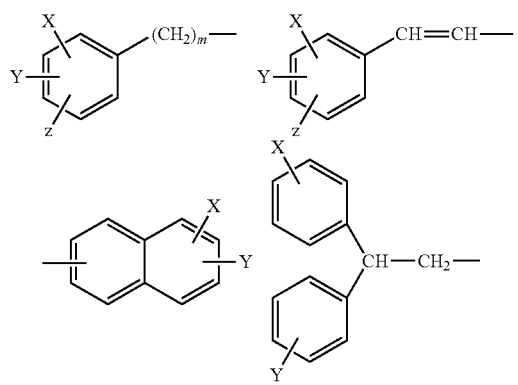

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, and m is 0, 1, 2, 3 or 4.

and $R^1$-$R^9$ and n are defined as above.

Furthermore, sulfonamide derivatives of general formula (Ia) are preferred, wherein A represents a heteroaryl radical selected from the group consisting of benzo[b]thiophenyl and imidazo[2,1-b]thiazolyl which may be substituted by 1, 2 is or 3 substituents selected from the group consisting of chlorine, methyl, phenyl and —O-phenyl and/or which may be bonded via a $C_{1-2}$ alkylene group, or a radical chosen from the group consisting of

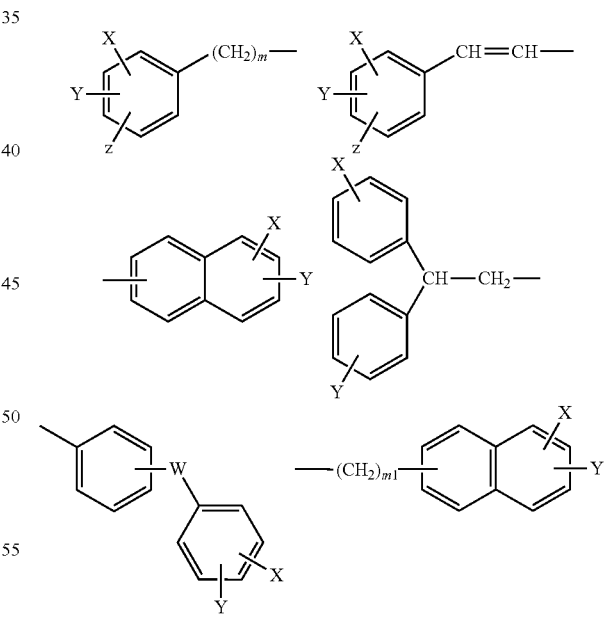

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a CH$_2$, O, S group or a NR$^{14}$ radical, wherein R$^{14}$ is hydrogen or a linear or branched C$_1$-C$_6$ alkyl, m is 0, 1, 2, 3 or 4 and m1 is 1 or 2, preferably 2, and R$^1$-R$^9$ and n are defined as above.

Furthermore sulfonamide derivatives of general formula (Ia) are preferred, wherein n is 0, 1, 2, 3 or 4; preferably n is 1 or 2; more preferably n is 2 and R$^1$ to R$^9$ and A are defined as above.

Furthermore, sulfonamide derivatives of general formula (Ib) are also preferred, wherein R$^2$, R$^3$, R$^5$, R$^6$ and R$^7$, identical or different, each represent hydrogen, a linear or branched C$_1$-C$_6$ alkyl radical, a linear or branched, optionally at least mono-substituted C$_1$-C$_6$ alkyl radical, a linear or branched, optionally at least mono-substituted C$_2$-C$_6$ alkenyl radical, or a linear or branched, optionally at least mono-substituted C$_2$-C$_6$ alkynyl radical, more preferably R$^2$, R$^3$, R$^5$, R$^6$ and R$^7$, identical or different, each represent hydrogen or a linear or branched, optionally at least mono-substituted C$_1$-C$_6$ alkyl radical, more preferably R$^2$, R$^3$, R$^5$, R$^6$ and R$^7$ each represent hydrogen or a C$_{1-2}$ alkyl radical and R$^1$, R$^4$, R$_8$, R$^9$, A and n are defined as above.

Sulfonamide derivatives of general formula (Ib) are also preferred, wherein R$^4$ represents hydrogen, a linear or branched, optionally at least mono-substituted C$_{1-C6}$ alkyl radical, a linear or branched, optionally at least mono-substituted C$_2$-C$_6$ alkenyl radical, a linear or branched, optionally at least mono-substituted C$_2$-C$_6$ alkynyl radical, more preferably that R$^4$ represents hydrogen or a linear or branched, optionally at least mono-substituted C$_1$-C$_6$ alkyl radical, even more preferably R$^4$ represents hydrogen or a C$_1$-C$_2$ alkyl radical and R$^1$-R$^3$, R$^5$-R$^9$, A and n are defined as above.

Furthermore, sulfonamide derivatives of general formula (Ib) are also preferred, wherein R$_8$ and R$^9$, identical or different, each represent hydrogen or a linear or branched, optionally at least mono-substituted C$_1$-C$_4$ alkyl radical, and R$^1$-R$^7$, A and n are defined as above.

Particularly preferred are sulfonamide derivatives of general formula (Ib) wherein R$^8$ and R$^9$, identical or different, each represent hydrogen or a C$_1$-C$_2$ alkyl radical, with the proviso that R$_8$ and R$^9$ are not hydrogen at the same time, and R$^1$-R$^7$, A and n are defined as above.

Furthermore, sulfonamide derivatives of general formula (Ib) are preferred, wherein A represents an optionally at least mono-substituted mono- or polycyclic aromatic ring system, wherein the ring(s) is/are 5- or 6-membered, which may be bonded via an optionally at least mono-substituted C$_1$-C$_6$ alkylene group, an optionally at least mono-substituted C$_2$-C$_6$ alkenylene group or an optionally at least mono-substituted C$_2$-C$_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

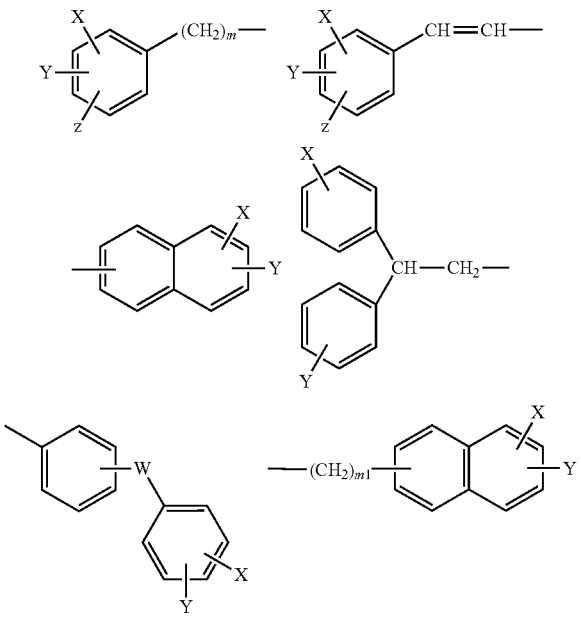

wherein X, Y, Z, independently from one another, each represent a radical selected from the group consisting of hydrogen, fluorine, chlorine, bromine, linear or branched C$_1$-C$_6$ alkyl, linear or branched C$_1$-C$_6$ alkoxy, linear or branched C$_1$-C$_6$ alkylthio, a trifluoromethyl radical, a cyano radical and a —NR$^{12}$R$^{13}$ radical, wherein R$^{12}$ and R$^{13}$, identical or different, each represent hydrogen or linear or branched C$_1$-C$_6$ alkyl, W represents a single chemical bond between the two rings, a CH$_2$, O, S group or a NR$^{14}$ radical, wherein R$^{14}$ is hydrogen or a linear or branched C$_1$-C$_6$ alkyl, m is 0, 1, 2, 3or 4and m1 is 1 or 2, preferably 2, and R$^1$-R$^9$ n are defined as above.

Furthermore, sulfonamide derivatives of general formula (Ib) are preferred, wherein A represents an optionally at least mono-substituted mono- or polycyclic aromatic ring system, wherein the ring(s) is/are 5- or 6-membered, which may be bonded via an optionally at least mono-substituted C$_1$-C$_6$ alkylene group, an optionally at least mono-substituted C$_2$-C$_6$ alkenylene group or an optionally at least mono-substituted C$_2$-C$_6$ alkynylene group, and/or wherein the ring(s) may contain at least one heteroatom as a ring member, more preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

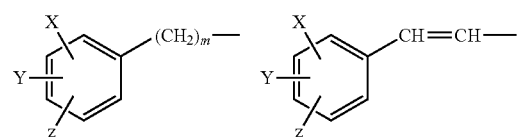

-continued

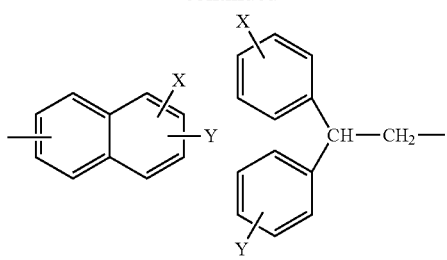

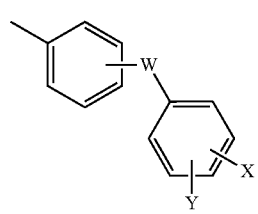

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —NR$^2$R$^{13}$ radical, wherein R$^{12}$ and R$^{13}$₁ identical or different, each represent hydrogen or linear or branched $C_1$-$C_6$alkyl, W represents a single chemical bond between the two rings, a CH$_2$, O, S group or a NR$^{14}$ radical, wherein R$^{14}$ is hydrogen or a linear or branched $C_1$-$C_6$ alkyl, and m is 0, 1, 2, 3 or 4.

and R$^1$-R$^9$ and n are defined as above.

Furthermore, sulfonamide derivatives of general formula (Ib) are preferred, wherein A represents a heteroaryl radical selected from the group consisting of benzo[b]thiophenyl and imidazo[2,1-b]thiazolyl which may be substituted by 1, 2 or 3 substituents selected from the group consisting of chlorine, methyl, phenyl and —O-phenyl and/or which may be bonded via a $C_{1-2}$ alkylene group, or a radical chosen from the group consisting of

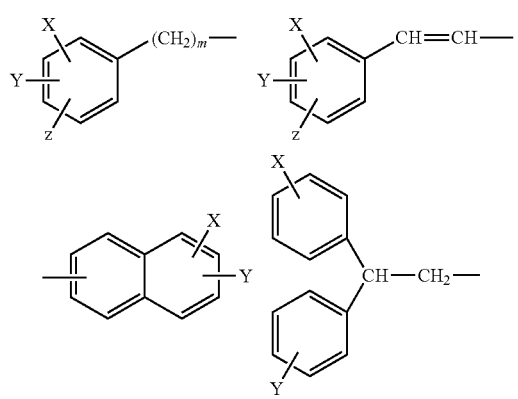

-continued

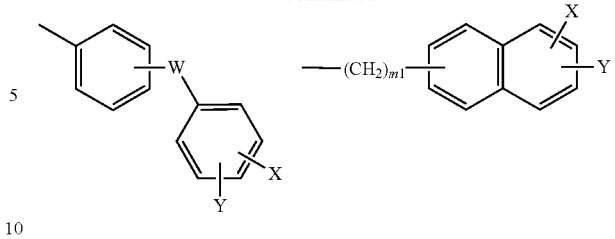

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —NR$^{12}$R$^{13}$ radical, wherein R$^{12}$ and R$^{13}$, identical or different, each represent hydrogen or linear or branched $C_1$-$C_6$alkyl, W represents a single chemical bond between the two rings, a CH$_2$, O, S group or a NR$^{14}$ radical, wherein R$^{14}$ is hydrogen or a linear or branched $C_1$-$C_6$ alkyl, m is 0, 1, 2, 3 or 4 and m1 is 1 or 2, preferably 2, and R$^1$-R$^9$ and n are defined as above. Furthermore sulfonamide derivatives of general formula (Ib) are preferred, wherein n is 0, 1, 2, 3 or 4; preferably n is 1 or 2; more preferably n is 2 and R$^1$ to R$^9$ and A are defined as above.

The most preferred compounds of general formula (Ib) are selected from the group consisting of

[1] N-[1-(2-dimethylaminoethyl)-1H-indole-4-yl]-5-chloro-3-methylbenzo[b]thiophene-2-sulfonamide,

[2] N-[1-(2-dimethylaminoethyl)-1H-indole-4-yl]-naphtalene-2-sulfonamide,

[3] N-[1-(2-dimethylaminoethyl)-1H-indole-4-yl]-naphtalene-1-sulfonamide,

[4] N-[1-(2-dimethylaminoethyl)-1H-indole-4-yl]4-phenyl-benzenesulfonamide,

[5] N-[1-(2-dimethylaminoethyl)-1H-indole-4-yl]-2-(naphtalene-1-yl)-ethanesulfonamide,

[6] N-[1-(2-dimethylaminoethyl)-1H-indole-4-yl]4-phenoxybenzenesulfonamide,

[7] N-[1-(2-dimethylaminoethyl)-1H-indole-4-yl]-3,5-dichlorobenzenesulfonamide and

[8] 6-chloro-N-[1-(2-dimethylaminoethyl)-1H-indol-4-yl]-imidazo[2,1-b]thiazole-5-sulfonamide and their corresponding salts and solvates.

Sulfonamide derivatives of general formula (Ic) are preferred, wherein R$^1$ represents a —NR$^8$R$^9$ radical or a saturated or unsaturated optionally at least mono-substituted 5- or 6-membered cycloaliphatic radical, which may optionally contain at least one heteroatom as a ring member and which may be condensed with a saturated or unsaturated, optionally at least mono-substituted mono- or bicyclic cycloaliphatic ring, which may optionally contain at least one heteroatom as a ring member, whereby the rings of the ring system are 5- or 6-membered, more preferably $R^1$ represents a —$NR^8R^9$ radical or a radical chosen from the group consisting of

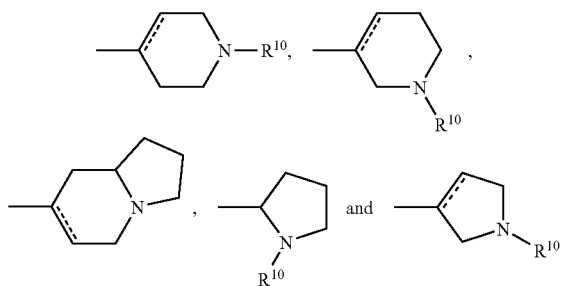

wherein, if present, the dotted line represents an optional chemical bond, and $R^{10}$ represents hydrogen, a linear or branched $C_1$-$C_6$ alkyl radical or a benzyl radical, preferably hydrogen or a $C_1$-$C_2$ alkyl radical and $R^2$-$R^9$, A and n are defined as above.

Sulfonamide derivatives of general formula (Ic) are also preferred, wherein $R^2$, $R^3$, $R^5$, $R^6$ and $R^7$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical, more preferably $R^2$, $R^3$, $R^5$, $R^6$ and $R^7$, identical or different, each represent hydrogen or a linear or branched, optionally at least mono-substituted $C_1$-$C_6$ alkyl radical, even more preferably $R^2$, $R^3$, $R_5$, $R^6$ and $R^7$ each represent hydrogen or a $C_{1-2}$ alkyl radical and $R^1$, $R^4$, $R^8$, $R^9$, A and n are defined as above.

Sulfonamide derivatives of general formula (Ic) are also preferred, wherein $R^4$ represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical more preferably $R^4$ represents hydrogen or a linear or branched, optionally at least mono-substituted $C_1$-$C_6$ alkyl radical, even more preferably $R^4$ represents hydrogen or a $C_1$-$C_2$ alkyl radical and $R^1$-$R^3$, $R^5$-$R^9$, A and n are defined as above.

Furthermore, sulfonamide derivatives of general formula (Ic) are also preferred, wherein $R_8$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical, a linear or branched, optionally at least mono-substituted $C_2$-$C_{10}$ alkynyl radical, or $R^8$ and $R^9$ together with bridging nitrogen atom form a saturated or unsaturated, optionally at least mono-substituted 5- or 6-membered heterocyclic ring which may contain at least one additional heteroatom as a ring member and/or which may be condensed with a saturated or unsaturated, optionally at least mono-substituted mono- or bicyclic cycloaliphatic ring, which may optionally contain at least one heteroatom as a ring member, whereby the rings of the ring system are 5- 6- or 7-membered and $R^1$-$R^7$, A and n are defined as above.

Particularly preferred are sulfonamide derivatives of general formula (Ic), wherein $R^8$ and $R^9$, identical or different, each represent hydrogen or a linear or branched $C_1$-$C_{10}$ alkyl radical, or $R^8$ and $R^9$ together with bridging nitrogen atom form a radical chosen from the group consisting of

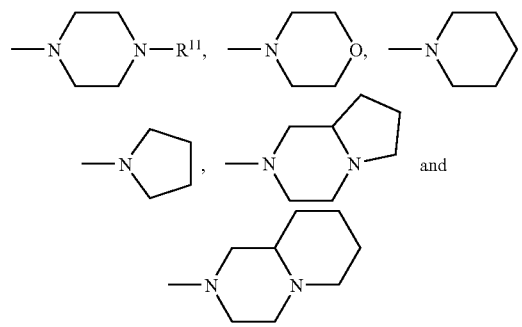

wherein $R^{11}$, if present, represents hydrogen, a linear or branched $C_1$-$C_6$ alkyl radical or a benzyl radical, preferably hydrogen, or a $C_1$-$C_2$ alkyl radical, and $R^1$-$R^9$, A and n are defined as above.

Furthermore, sulfonamide derivatives of general formula (Ic) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

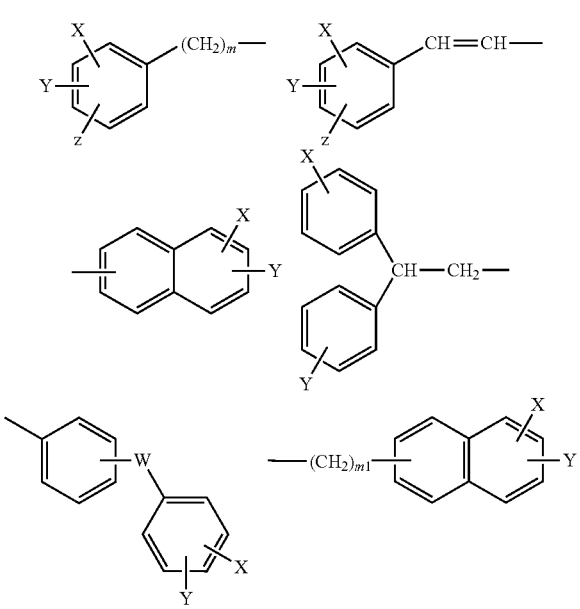

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-C6 alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore, sulfonamide derivatives of general formula (Ic) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group, and/or wherein the ring(s) may contain at least one heteroatom as a ring member, more preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

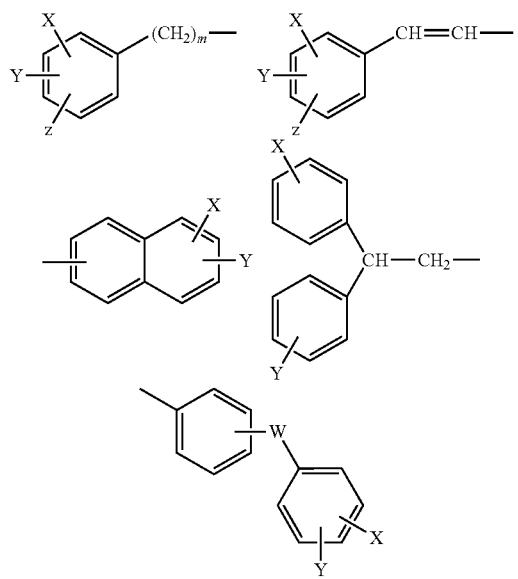

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, and m is 0, 1, 2, 3 or 4.

and $R^1$-$R^9$ and n are defined as above.

Furthermore, sulfonamide derivatives of general formula (Ic) are preferred, wherein A represents a heteroaryl radical selected from the group consisting of benzo[b]thiophenyl and imidazo[2,1-b]thiazolyl which may be substituted by 1, 2 or 3 substituents selected from the group consisting of chlorine, methyl, phenyl and —O-phenyl and/or which may be bonded via a $C_{1-2}$ alkylene group, or a radical chosen from the group consisting of

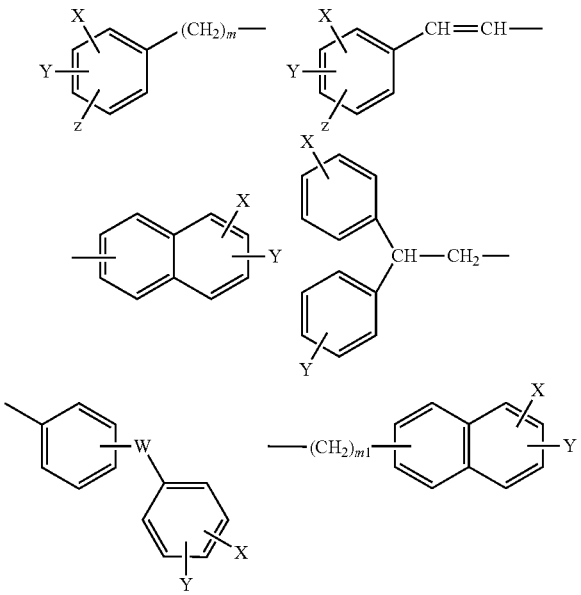

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$ identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore sulfonamide derivatives of general formula (Ic) are preferred, wherein n is 0, 1, 2, 3 or 4; preferably n is 1 or 2; more preferably n is 2 and $R^1$ to $R^9$ and A are defined as above.

Yet another aspect of the present invention are compounds of general formula (Ic),

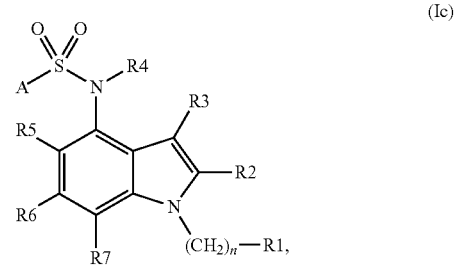

(Ic)

wherein $R^1$ represents a —$NR^8R^9$ radical, $R^2$, $R^3$, $R^5$, $R^6$ and $R^7$ each represent hydrogen, $R^4$ represents hydrogen, $R^8$ and $R^9$, identical or different, each represent methyl, ethyl, n-propyl, iso-propyl, more preferably methyl, and A represents an aryl or heteroaryl radical selected from the group consisting of phenyl, naphthyl, benzo[b]thiophenyl and imidazo[2,1-b]thiazolyl which may be substituted by 1, 2 or 3 substituents selected from the group consisting of chlorine, methyl, phenyl and —O-phenyl and/or which may be bonded via a $C_{1-2}$ alkylene group, and n is 2;

optionally in form of one of its stereoisomers, preferably enantiomers or diastereomers, its racemate or in form of a mixture of at least two of its stereoisomers, preferably enantiomers or diastereomers, in any mixing ratio, or a salt thereof, preferably a corresponding, physiologically acceptable salt thereof, or a corresponding solvate thereof.

The most preferred compounds of general formula (Ic) are selected from the group consisting of

[1] N-[1-(2-dimethylaminoethyl-1H-indole-4-yl]-5-chloro-3-methylbenzo[b]thiophene-2-sulfonamide,

[2] N-[1-(2-dimethylaminoethyl)-1H-indole-4-yl]-naphtalene-2-sulfonamide,

[3] N-[1-(2-dimethylaminoethyl)-1H-indole4-yl]-naphtalene-1-sulfonamide,

[4] N-[1-(2-dimethylaminoethyl)-1H-indole-4-yl]-4-phenylbenzenesulfonamide,

[5] N-[1-(2-dimethylaminoethyl)-1H-indole-4-yl]-2-(naphtalene-1-yl)-ethanesulfonamide,

[6] N-[1-(2-dimethylaminoethyl)-1H-indole-4-yl]4-phenoxybenzenesulfonamide,

[7] N-[1-(2-dimethylaminoethyl)-1H-indole4-yl]-3,5-dichlorobenzenesulfonamide and

[8] 6-chloro-N-[1-(2-dimethylaminoethyl)-1H-indol-4-yl]-imidazo[2,1-b]thiazole-5-sulfonamide and their corresponding salts and solvates.

The present invention likewise refers to the salts, preferably the physiologically acceptable salts of the compounds of general formula (Ia) and/or (Ib) and/or of general formula (Ic), preferably the addition salts of mineral acids, more preferably of hydrochloric acid, hydrobromic acid acid, phosphoric acid, sulphuric acid, nitric acid, and the salts of organic acids, more preferably of citric acid, maleic acid acid, fumaric acid, tartaric acid or their derivatives, p-toluenesulphonic acid, methanesulphonic acid, camphorsulphonic acid, etc.

Below, the expression sulfonamide derivatives refers to the general formula (I), to one or more compounds of general formula (Ia) and/or to one or more compounds of general formula (Ib) and/or to one or more compounds of general formula (Ic), respectively, and optionally in form of one of their stereoisomers, preferably enantiomers or diastereomers, their racemate, or in form of a mixture of at least two of their stereoisomers, preferably enantiomers or diastereomers, in any mixing ratio, or a salt thereof, preferably a corresponding physiologically acceptable salt thereof, or a corresponding solvate thereof.

Another aspect of the present invention consists of a process for obtaining the new derivatives of general formula (I), wherein $R^1$-$R^9$, n and A have the previously indicated meaning, according to which at least one compound of general formula (II),

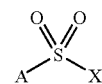

(II)

wherein A has the previously mentioned meaning, and X is an acceptable leaving group, preferably an halogen atom, more preferably chlorine; is reacted with at least one substituted 4-aminoindole of general formula (III)

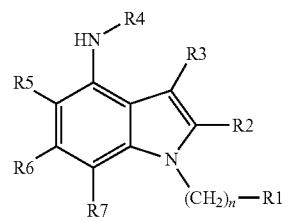

(III)

wherein $R^1$-$R^7$ and n have the previously indicated meaning, or one of their suitable protected derivatives, and, if necessary, the protective groups are removed in order to obtain the corresponding sulfonamide derivative of formula (I), which may be purified and/or isolated via conventional methods known in the prior art.

The reaction between the compounds of general formula (III) and (III) is usually carried out in the presence of an organic reaction medium, preferably in the presence of dialkyl ether, more preferably diethyl ether or a cyclic ether, more preferably tetrahydrofuran or dioxane, an halogenated organic hydrocarbon, more preferably methylene chloride or chloroform, an alcohol, more preferably methanol or ethanol, a dipolar aprotic solvent, more preferably acetonitrile, pyridine or dimethylformamide, or any other suitable reaction medium. Naturally, mixtures of at least two of the classes of the mentioned compounds or at least two compounds of one class may also be used.

The reaction is preferably carried out in the presence of a suitable base, for example, an inorganic base, more preferably alkaline metal hydroxides and alkaline metal carbonates, or in the presence of an organic base, more preferably triethylamine, N-ethyldiisopropylamine or pyridine.

The most suitable reaction temperatures range from 0° C. to room temperature, that is, approximately 25° C., and the reaction time is preferably from 5 minutes to 24 hours.

The resulting sulfonamide derivative of general formula (I) may be purified and/or isolated according to conventional methods known in the prior art.

Preferably, the sulfonamide derivatives of general formula (I) may be isolated by evaporating the reaction medium, adding water and, if necessary, adjusting the pH so that a solid which may be isolated by filtration is obtained; or the sulfonamide derivatives may be extracted with a water immiscible solvent, preferably chloroform, and be purified by chromatography or recrystallization of a suitable solvent.

The compounds of general formula (II) are commercially available, or they may be prepared according to standard methods known in the prior art, for example by methods similar to those described in the literature [E. E. Gilbert, Synthesis, 1969, 1, 3]. The compounds of general formula (III) may also be prepared according to standard methods known in the prior art, for example by methods similar to those described in: [Abou-Gharbia, Magid; Patel, Usha; Tokolics, Joseph; Freed, Meier. European Journal of Medicinal Chemistry (1988), 23(4), 373-7]. The respective literature descriptions are incorporated by reference and form part of the disclosure.

Another aspect of the present invention consists in a process for preparing the new sulfonamide derivatives of general formula (I), wherein $R^1$-$R^3$, $R^5$-$R^9$, n and A have the previously indicated meaning and $R^4$ is an alkyl radical, preferably a linear or branched, optionally at least mono-substituted $C_1$-$C_6$ alkyl radical, by alkylation of a sulfonamide derivative of general formula (I), wherein $R^1$-$R^3$, $R^5$-$R^7$, n and A have the previously indicated meaning, and $R^4$ is an hydrogen atom, with an alkyl halogenide or a dialkyl sulfate.

The alkylation reaction is carried out preferably in the presence of a suitable base, more preferably in the presence of alkaline metal hydroxides and alkaline metal carbonates, metal hydrides, metal alkoxides, even more preferably sodium methoxide or potassium tert-butoxide, organometallic compounds, even more preferably butyllithium or tert-butyllithium, in the presence of an organic reaction medium, more preferably dialkyl ether, even more preferably diethyl ether, or a cyclic ether, even more preferably tetrahydrofuran or dioxane, an hydrocarbon, even more preferably toluene, an alcohol, even more preferably methanol or ethanol, a dipolar aprotic solvent, even more preferably acetonitrile, pyridine or dimethylformamide, or any other suitable reaction medium. Naturally, mixtures of at least two of the classes of the mentioned compounds or at least two compounds of one class may also be used.

The most suitable reaction temperatures range from 0° C. to the boiling temperature of the reaction medium, and the reaction times are preferably from 1 to 24 hours.

Preferably, the resulting sulfonamide derivative of general formula (I) may be isolated by filtration, concentrating the filtrate under reduced pressure, adding water and, if necessary, adjusting the pH so that a solid which may be isolated by filtration is obtained; or the sulfonamide derivatives may be extracted with a water immiscible solvent, preferably chloroform, and be purified by chromatography or recrystallization of a suitable solvent.

The salts, preferably pharmaceutically acceptable salts of the compounds of general formula (I), may be prepared by means of conventional methods known in the prior art, preferably by reaction with a mineral acid, more preferably by reaction with hydrochloric acid, hydrobromic acid, phosphoric acid acid, sulphuric acid or nitric acid, or by reaction with organic acids, more preferably by reaction with citric acid, maleic acid, fumaric acid acid, tartaric acid, or their derivatives, p-toluenesulphonic acid, methanesulphonic acid, camphorsulphonic acid, etc., in a suitable solvent, preferably methanol, ethanol, diethyl ether, ethyl acetate, acetonitrile or acetone, and obtaining the resulting salts by using the usual techniques for the precipitation or crystallization of the corresponding salts.

The preferred physiologically acceptable salts of the sulfonamide derivatives of general formula (I) are the addition salts of mineral acids, more preferably of hydrochloric acid, hydrobromic acid, phosphoric acid, sulphuric acid acid or nitric acid, and the addition salts of organic acids, more preferably citric acid, maleic acid, fumaric acid, tartaric acid, or their derivatives, p-toluenesulphonic acid, methanesulphonic acid, camphorsulphonic acid, etc.

The solvates, preferably the physiologically acceptable solvates, more preferably hydrates, of the sulfonamide derivatives of general formula (I) or of the corresponding physiologically acceptable salts, may be prepared by methods known in the prior art.

During some of the synthetic sequences described or in the preparation of the suitable reagents used, it may be necessary and/or desirable to protect sensitive or reactive groups in some of the molecules used. This may be carried out via the use of conventional protective groups preferably those described in the literature [Protective groups in Organic Chemistry, ed. J. F. W. McOmie, Plenum Press, 1973; T. W. Greene & P. G. M. Wuts, Protective Groups in Organic Chemistry, John Wiley & Sons, 1991]. The protective groups may be removed in the suitable subsequent stage by methods known in the prior art. The respective literature descriptions are incorporated by reference and form part of the disclosure.

If the sulfonamide derivatives of general formula (I) are obtained in form of a mixture of stereoisomers, preferably enantiomers or diastereomers, said mixtures may be separated via standard processes known in the prior art, for example chromatographic methods or crystallization with chiral agents.

Another aspect of the present invention is a medicament comprising at least one indol-4-yl sulfonamide derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally one or more pharmaceutically acceptable adjuvants.

This medicament is suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-$HT_6$ serotonin receptor in humans and/or in animals, preferably in mammals, more preferably in humans.

Another aspect of the present invention is a medicament comprising at least one indol-4-yl sulfonamide derivative of general formula (Ia), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally one or more pharmaceutically acceptable adjuvants.

This medicament is suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and Multiple Sclerosis, schizophrenia, psychosis or infantile hyperkinesia (ADHD, attention deficit/hyperactivity disorder) in humans and/or in animals, preferably in mammals, more preferably in humans, more suitable preferably for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome.

Another aspect of the present invention is a medicament comprising at least one indol-4-yl sulfonamide derivative of general formula (Ib), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally one or more pharmaceutically acceptable adjuvants.

This medicament is suitable for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans,
more suitable for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and Multiple Sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans.

Another aspect of the present invention is a medicament comprising at least one indol-4-yl sulfonamide derivative of general formula (Ic), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally one or more pharmaceutically acceptable adjuvants.

This medicament is suitable for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans.

The medicament obtained according to the present invention is particularly suitable for the administration to mammals, including humans. The medicament may preferably be administered to all age groups, namely, children, adolescents and adults.

Another aspect of the present invention is the use of at least one sulfonamide derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and Multiple Sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans.

Another aspect of the present invention is the use of at least one sulfonamide derivative of the previous general formula (Ia), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and Multiple Sclerosis, schizophrenia, psychosis or infantile hyperkinesia (ADHD, attention deficit/hyperactivity disorder) and other disorders mediated by the $5\text{-}HT_6$ serotonin receptor in humans and/or in animals, preferably in mammals, more preferably in humans, more preferably for the manufacture of a medicament for $5\text{-}HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome in humans and/or in animals, preferably in mammals, more preferably in humans.

Another aspect of the present invention is the use of at least one sulfonamide derivative of the previous general formula (Ib), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for $5\text{-}HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and Multiple Sclerosis, schizophrenia, psychosis or infantile hyperkinesia (ADHD, attention deficit/hyperactivity disorder) and other disorders mediated by the $5\text{-}HT_6$ serotonin receptor in humans and/or in animals, preferably in mammals, more preferably in humans, more preferably the manufacture of a medicament for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and Multiple Sclerosis, schizophrenia, psychosis or infantile hyperkinesia (ADHD, attention deficit/hyperactivity disorder) in humans and/or in animals, preferably in mammals, more preferably in humans.

Another aspect of the present invention is the use of at least one sulfonamide derivative of general formula (Ic), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for $5\text{-}HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and Multiple Sclerosis, schizophrenia, psychosis or infantile hyperkinesia (ADHD, attention deficit/hyperactivity disorder) and other disorders mediated by the $5\text{-}HT_6$ serotonin receptor in humans and/or in animals, preferably in mammals, more preferably in humans.

The preparation of the corresponding pharmaceutical compositions as well as of the formulated medicaments may be carried out via conventional methods known in the prior art, for example, based on the indices of "Pharmaceutics: The Science of Dosage Forms", Second Edition, Aulton, M. E. (ED. Churchill Livingstone, Edinburgh (2002)); "Encyclopedia of Pharmaceutical Technology", Second Edition, Swarbrick, J. and Boylan, J. C. (Eds.), Marcel Dekker, Inc. New York (2002); "Modern Pharmaceutics", Fourth Edition, Banker G. S. and Rhodes C. T. (Eds.) Marcel Dekker, Inc. New York (2002), and "The Theory and Practice of Industrial Pharmacy", Lachman L., Lieberman H. and Kanig J. (Eds.), Lea & Febiger, Philadelphia (1986). The respective literature descriptions are incorporated as a reference and are part of this disclosure.

The pharmaceutical compositions, as well as the formulated medicaments prepared according to the present invention, may, in addition to at least one sulfonamide derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, comprise other conventional auxiliary substances known In the prior art, preferably excipients, fillers, solvents, diluents, dyes, coating agents, matrix forming agents and/or binders. As the skilled persons in the art also knows, the choice of the auxiliary substances and the amounts thereof depend on the intended administration route, for example, rectal, intravenous, intraperitoneal, intramuscular, intranasal, oral, buccal or topical.

Medicaments suitable for oral administration are, for example, tablets, coated tablets, capsules or multiparticulates, preferably granules or pellets, optionally subjected to compression in tablets, filled in capsules or suspended in solutions, suspensions or suitable liquids.

Medicaments suitable for parenteral, topical or inhalatory administration may preferably be chosen from the group consisting of solutions, suspensions, quickly reconstitutable dry preparations and also sprays.

Medicaments suitable for oral or percutaneous use may release the sulfonamide compounds of general formula (I) in a sustained manner, the preparation of these sustained release medicaments generally being known in the prior art.

Suitable sustained release forms, as well as the materials and methods for the preparation thereof, are known in the art, for example from the indices of "Modified-Release Drug Delivery Technology", Rathbone, J. JI, Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York (2000); "Controlled Drug Delivery", Vol. 1, Basic Concepts, Bruck, S. D. (Ed.), CRD Press, Inc., Boca Raton (1983), and by Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728. The respective literature references are incorporated by reference and form part of the disclosure.

The medicament of the present invention may also have at least one enteric coating, which dissolves according to the pH. As a result of this coating, the medicament may pass through the stomach without dissolving, and the compounds of general formula I are only released in the intestinal tract. The enterc coating preferably dissolves at a pH of between 5 and 7.5. The materials and methods suitable for preparing enteric coatings are also known in the prior art.

Typically, the pharmaceutical compositions and the medicaments comprise from 1 to 60% by weight of one or more sulfonamide derivatives of general formula (I), and from 40 to 99% by weight of one or more excipients.

The drug substance amount to be administered to the patient varies according to the patent's weight, the administration route, the indication and the severity of the disorder. Usually from 1 mg to 2 g of at least one sulfonamide derivative of general formula (I) are administered per patient per day. The total daily dose may be administered to the patient in one or more doses.

Pharmaceutical Methods:
Binding to the $5Ht_6$ Serotonin Receptor

HEK-293 cell membranes expressing the recombinant human $5HT_6$ receptor were supplied by Receptor Biology. The receptor concentration in said membranes is 2.18 pmol/mg of protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipshychotic Agents to 5-Hydroxytryptamine-6 and Hydroxytryptamine-7 Receptors. *The Journal of Pharmacology and Experimental Therapeutics,* 1994, 268, 1403], with slight modifications. The commercial membrane is diluted (1:40 dilution) with the binding buffer: 50 mM Tris-HCl, 10 mM $MgCl_2$, 0.5 mM EDTA (pH 7.4). The radioligand used is [$^3$H]-LSD at a concentration of 2.7 nM, the final volume being 200 µl. Incubation begins by adding 100 µl of the membrane suspension (≈22.9 µg of membrane protein), and is prolonged for 60 minutes at a temperature of 37° C. Incubation ends by quick filtration in a Harvester Brandel Cell through fiberglass filters of the Schleicher & Schuell GF 3362 trademark, pretreated with a 0.5% polyethyleneimine solution. The filters are washed three times with three milliliters of 50 mM Tris HCl buffer, pH 7.4. The filters are transferred to vials and 5 ml of Ecoscint H. liquid scintillation cocktail are added to each vial. The vials are left to equilibrate for several hours prior to their counting in a 1414 Wallac Winspectral scintillation counter. The non-specific binding is determined in the presence of 100 µM of serotonin. The assays are carried out in triplicate. The inhibition constants ($K_i$, nM) are calculated by non-linear regression analysis using the EBDA/LIGAND program [Munson and Rodbard, *Analytical Biochemistry,* 1980, 107, 220].

The respective literature descriptions are incorporated by reference and form part of the disclosure.

Measurements Of Food Ingestion (Behavioural Model)

Male W rats (200-270 g) from Harlan, S. A. are used. The animals are acclimatized to the housings during at least 5 days prior to being subjected to any treatment. During this period, the animals are housed (in groups of five) in translucent cages and have free access to water and food. The animals are housed in individual cages at least 24 hours prior to starting the treatment.

The acute effect of the sulfonamide derivatives of formula (I) used inventively on food ingestion in rats in fasting conditions is then determined as follows:

The rats are kept in fasting conditions for 23 hours in their individual cages. After this period, the rats are orally or intraperitoneally treated with a dose of a composition containing a sulfonamide derivative of general formula (I) or a corresponding composition (vehicle) without said sulfonamide derivative. Immediately after this, the rat is left with pre-weighed food and the accumulated food intake is measured after 1, 2, 4 and 6 hours.

This food ingestion measuring method is also described in publications of Kask et al., *European Journal of Pharmacology* 414 (2001), 215-224, and Turnbull et al., *Diabetes*, Vol. 51, August, 2002. The respective bibliographic descriptions are incorporated as a reference and they form part of the disclosure.

The preparation of new compounds according to the invention is indicated in the following examples. The affinity for the $5HT_6$ serotonin receptor, as well as the galenic formulas applicable to the compounds of the invention, is also described. The examples indicated below, given as an illustrative example, should in no way limit the scope of the invention.

EXAMPLES

Example 1

Preparation of N-[1-(2-dimethylaminoethyl)-1H-indole-4-yl]-5-chloro-3-methyl-benzo[b]thiophene-2-sulfonamide 185.5 mg (0.66 mMol) of 5-chloro-3-methyl-benzo[b]thiophene-2-sulfonyl chloride were added to a solution of 122 mg (0.6 mMol) of 4-amino-3-(2-dimethylaminoethyl)-1H-indole in 2 ml of dimethylformamide and 116 mg of N-ethyldiisopropylamine. The reaction mixture was stirred at the room temperature for 20 hours. Then it was evaporated to dryness, slightly alkalinized with sodium bicarbonate solution and extracted with chloroform. The organic phase was repeatedly washed with water and saturated solution of sodium bicarbonate, it was separated and dried with anhydrous sodium sulfate. The organic solution was evaporated to dryness and the resulting solid was purified by chromatography, obtaining 111 mg (42%) of N-[1-(2-dimethylaminoethyl)-1H-indole-4-yl]-5-choloro-3-methyl-benzo[b]thiophene-2-sulfonamide as a creamy solid.

Example 2

Preparation of N-[1-(2-dimethylaminoethyl)-1H-indole-4-yl]-naphtalene-2-sulfonamide 121 mg (51%) of the mentioned compound were obtained from 122 mg (0.6 mMol) of 4-amino-1-(2-dimethylaminoethyl)-1H-indole and 149.5 mg (0.66 mMol) of naphtalene-2-sulfonyl chloride, via the process described in the Example 1, as a creamy solid.

Example 3

Preparation of N-[1-(2-dimethylaminoethyl)-1H-indole-4-yl]-naphtalene-1-sulfonamide 130 mg (55%) of the mentioned compound are obtained from 122 mg (0.6 mMol) of 4-amino-1-(2-dimethylaminoethyl)-1H-indole and 149.5 mg (0.66 mMol) of naphtalene-1-sulfonyl chloride, via the process described in the Example 1, as a creamy solid.

Example 4

Preparation of N-[1-(2-dimethylaminoethyl)-1H-indole-4-yl]-4phenylbenzenesulfonamide 107 mg (42%) of the mentioned compound were obtained from 122 mg (0.6 mMol) of 4-amino-1-(2-dimethylaminoethyl)-1H-indole and 169 mg (0.66 mMol) of 4-phenylbenzenesulfonyl chloride, via the process described in the Example 1, as a creamy solid.

Example 5

Preparation of N-[1-(2-dimethylaminoethyl)-1H-indole-4-yl]-2-(naphtalene-1-yl)-ethanesulfonamide 52 mg (21%) of the mentioned compound were obtained from 122 mg (0.6 mMol) of 4-amino-1-(2-dimethylaminoethyl)-1H-indole and 168 mg (0.66 mMol) of 2-(naphtalene-1-yl)-ethanesulfonyl chloride, via the process described in the Example 1, as a yellowish solid.

Example 6

Preparation of N-[1-(2-dimethylaminoethyl)-1H-indole-4-yl]-4-phenoxybenzenesulfonamide 220 mg (84%) of the mentioned compound were obtained from 122 mg (0.6 mMol) of 4-amino-1-(2-dimethylaminoethyl)-1H-indole and 177 mg (0.66 mMol) of 4-phenoxybenzenesulfonyl chloride, via the process described in the Example 1, as a oil.

Example 7

Preparation of N-[1-(2-dimethylaminoethyl)-1H-indole-4-yl]-3,5-dichlorobenzenesulfonamide 93 mg (38%) of the mentioned compound are obtained from 122 mg (0.6 mMol) of 4-amino-1-(2-dimethylaminoethyl)-1H-indole and 162 mg (0.66 mMol) of 3,5-dichlorobenzenesulfonyl chloride, via the process described in Example 1, as a creamy solid.

Example 8

Preparation of 6-chloro-N-[1-(2-dimethylaminoethyl)-1H-indol-4-yl]-imidazo[2,1-b]thiazole-5-sulfonamide 100 mg (39&) of the mentioned compound are obtained from 122 mg (0.6 mMol) of 4-amino-1-(2-dimethylaminoethyl)-1H-indole and 170 mg (0.66 mMol) of 6-chloro-imidazo[2,1-b]-thiazole-5-sulfonyl chloride via the process described is in Example 1 as a creamy solid.

The yields are indicative and no added effort was made to improve them.

The melting point and spectroscopic data for identifying some of the compounds of the present invention are indicated in the following table.

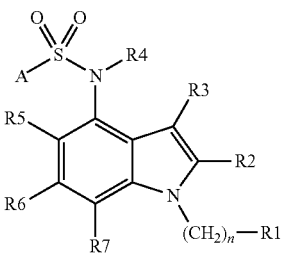

| Ex | $R_1$ | $R_2$ | $R_3$ | $R_4$ | $R_5$ | $R_6$ | $R_7$ | n | A | m.p. °C. | IR cm$^{-1}$ | $^1$H-NMR (300 MHz), δ (solvent) |
|----|-------|-------|-------|-------|-------|-------|-------|---|---|----------|--------------|-----------------------------------|
| 1 | $(CH_3)_2N-$ | H | H | H | H | H | H | 2 | ![5-chloro-2,3-dimethylbenzothiophene] | 78-80 | 3430, 2951, 1492, 1328, 1156, 1115, 1079, 859, 750, 649, 569. | 2.10 (s, 6H); 2.28 (s, 3H); 2.50 (m, 2H); 4.14 (t, 2H, J=6.3 Hz); 6.43 (d, 1H, J=2.0 Hz); 6.92 (d, 1H, J=7.5 Hz); 7.00 (t, 1H, J=7.7 Hz); 7.17 (d, 1H, J=2.2 Hz); 7.25 (d, 1H, J=7.5 Hz); 7.49 (d, 1H, J=8.4 Hz); 7.85 (s, 1H); 7.99 (d, 1H, J=8.5 Hz). (DMSO-d6) |
| 2 | $(CH_3)_2N-$ | H | H | H | H | H | H | 2 | ![2-methylnaphthalene] | 156-158 | 3448, 2821, 1492, 1314, 1238, 1158, 1127, 1075, 1009, 752, 656, 645, 554, 543, 484. | 2.08 (s, 6H); 2.48 (m, 2H); 4.10 (t, 2H, J=6.6 Hz); 6.58 (d, 1H, J=3.1 Hz); 6.85-6.96 (m, 2H); 7.15 (d, 1H, J=7.8 Hz); 7.19 (d, 1H, J=3.1 Hz); 7.54-7.68 (m, 2Hz); 7.83 (dd, 1H, J=8.6 Hz, J'=1.8 Hz); 7.94 (d, 1H, J=8.1 Hz). (DMSO-d6) |

-continued

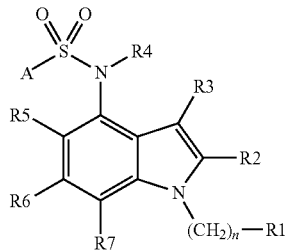

| Ex | R₁ | R₂ | R₃ | R₄ | R₅ | R₆ | R₇ | n | A | m.p. °C. | IR cm⁻¹ | ¹H-NMR (300 MHz), δ (solvent) |
|---|---|---|---|---|---|---|---|---|---|---|---|---|
| 3 | (CH₃)₂N— | H | H | H | H | H | H | 2 | 1-methylnaphthalene | 169-172 | 3279, 2943, 1403, 1318, 1162, 1132, 1003, 767, 745. | 2.08 (s, 6H); 2.46 (m, 2H); 4.07 (t, 2H, J=6.7 Hz); 6.45 (d, 1H, J=3.2 Hz); 6.81 (d, 1H, J=6.8 Hz); 6.88 (t, 1H, J=7.7 Hz); 7.09 (d, 1H, J=8.2 Hz); 7.12 (d, 1H, J=3.2 Hz); 7.52 (m, 1H); 7.62 (m, 1Hz); 7.70 (m, 1H); 8.01 (d, 1H, J=8.2 Hz); 8.11 (m, 2H), 8.87 (d, 1H, J=8.4 Hz). (DMSO-d6) |
| 4 | (CH₃)₂N— | H | H | H | H | H | H | 2 | 4-methylbiphenyl | 137-140 | 3262, 2943, 1492, 1330, 1160, 1096, 750, 670, 590, 531. | 2.10 (s, 6H); 2.51 (m, 2H); 4.14 (t, 2H, J=6.6 Hz); 6.61 (d, 1H, J=3.0 Hz); 6.90 (d, 1H, J=7.0 Hz); 6.97 (t, 1H, J=7.8 Hz); 7.19 (d, 1H, J=7.8 Hz); 7.23 (d, 1H, J=3.2 Hz); 7.36-7.69 (m, 3H); 7.65 (d, 2H, J=6.8 Hz); 7.76 (AB sys, 2H, J=8.6 Hz); 7.82 (AB sys, 2H, J=8.5 Hz,). (DMSO-d6) |
| 5 | (CH₃)₂N— | H | H | H | H | H | H | 2 | 1-propylnaphthalene | 47-54 | 3430, 3255, 2941, 2760, 1492, 1322, 1150, 748. | 2.16 (s, 6H); 2.59 (m, 2H); 3.35 (m, 4H); 4.24 (t, 2H, J=6.3 Hz); 6.89 (m, 1H, J=3.1 Hz); 7.05-7.11 (m, 2H); 7.22 (m, 1H); 7.28-7.38 (m, 4H); 7.41 (m, 2H); 7.74 (d, 1H, J=7.18 Hz); 7.86 (d, 1H, J=8.2 Hz). (DMSO-d6) |
| 6 | (CH₃)₂N— | H | H | H | H | H | H | 2 | 4-phenoxytoluene | oil | 2944, 2776, 1488, 1343, 1244, 1156, 1094, 751, 695 | 2.12 (s, 6H); 2.52 (m, 2H); 4.15 (t, 2H, J=6.5 Hz); 6.51 (d, 1H, J=3.0 Hz); 6.85 (d, 1H, J=7.6 Hz); 6.97 (m, 3H); 7.03 (d, 2H, J=7.6 Hz); 7.20 (d, 2H, J=8.1 Hz); 7.24 (d, 1H, J=3.2 Hz); 7.42 (t, 2H, J=7.9 Hz); 7.70 (d, 2H, J=8.9 Hz). (DMSO-d6) |
| 7 | (CH₃)₂N— | H | H | H | H | H | H | 2 | 3,5-dichlorotoluene | 113-118 | 3255, 3072, 2935, 1570, 1492, 1340, 1169, 1138, 803, 747, 670, 594. | 2.12 (s, 6H); 2.54 (t, 2H, J=6.6); 4.17 (t, 2H, J=6.5 Hz); 6.42 (d, 1H, J=3.1 Hz); 6.82 (d, 1H, J=7.6 Hz); 7.02 (t, 1H, J=8.0 Hz); 7.26-7.30 (m, 2H); 7.63 (d, 2H, J=1.9 Hz); 7.86 (t, 1H, J=1.8 Hz). (DMSO-d6) |
| 8 | (CH₃)₂N— | H | H | H | H | H | H | 2 | 6-chloro-5-methylimidazo[2,1-b]thiazole | 95-100 | | 2.15 (s, 6H); 2.56 (t, 2H, J=6.2 Hz); 4.17 (t, 2H, J=6.6 Hz); 6.31 (d, 1H, J=2.8 Hz); 6.89 (d, 1H, J=7.3 Hz); 7.01 (m, 1H); 7.21 (d, 1H, J=3.0 Hz); 7.27 (d, 1H, 8.0 Hz); 7.49 (d, 1H, J=4.4 Hz); 7.72 (d, 1H, J=4.4 Hz). (DMSO-d6) |

Pharmaceutical Data:

Binding of the new compounds of general formula (Ia and Ib and Ic) to the $5\text{-HT}_6$ receptor was determined as previously described.

The binding results for some of the compounds of the present invention are indicated in the following table:

TABLE

| Example | % Inhibition $10^{-6}$ M |
|---|---|
| 1 | 83.9 |
| 2 | 104.3 |
| 3 | 94.8 |
| 4 | 46.6 |
| 5 | 98.1 |
| 6 | 55.8 |
| 7 | 72.3 |

The daily posology in human medicine is comprised between 1 milligram and 2 grams of medicinal product which may be administered in one or several doses. The compositions are prepared under forms that are compatible with the administration route used, preferably tablets, coated tablets, capsules, suppositories, solutions or suspensions. These compositions are prepared via known methods and comprise from 1 to 60% by weight of the drug substance (compound of general formula I), and 40 to 99% by weight of the suitable pharmaceutical vehicle compatible with the medicament substance and the physical form of the composition used.

The formula of a tablet containing a product of the invention is provided by way of example:

Example of formula per tablet:

| | |
|---|---|
| Example 1 | 5 mg |
| Lactose | 60 mg |
| Crystalline cellulose | 25 mg |
| Povidone K 90 | 5 mg |
| Pregelatinized starch | 3 mg |
| Colloidal silicon dioxide | 1 mg |
| Magnesium stearate | 1 mg |
| Total weight per tablet | 100 mg |

The invention claimed is:

1. A sulfonamide compound of general formula (Ia),

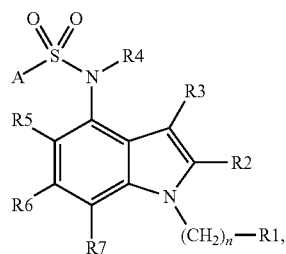

wherein
$R^1$ represents a $-NR^8R^9$ radical or a saturated or unsaturated, optionally at least mono-substituted cycloaliphatic radical, which may contain at least one heteroatom selected from nitrogen, sulphur and oxygen as a ring member and/or which may be condensed with a saturated or unsaturated, optionally at least mono-substituted, optionally at least one heteroatom selected from nitrogen, sulphur and oxygen as a ring member containing mono- or bicyclic cycloaliphatic ring system, wherein each of the substituents may be chosen from hydroxyl, fluorine, chlorine, bromide, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, $R^2$, $R^3$, $R^5$, $R^6$ and $R^7$, identical or different, each represent hydrogen, halogen, nitro, alkoxy, cyano, a saturated or unsaturated, linear or branched, aliphatic radical optionally at least mono-substituted by hydroxy, fluorine, chlorine, bromide or trifluoromethyl; or a phenyl or a heteroaryl radical $R^4$ is hydrogen or a saturated or unsaturated, linear or branched, aliphatic radical optionally at least mono-substituted by hydroxy, fluorine, chlorine, bromide or trifluoromethyl, $R^8$ and $R^9$, identical or different, each represent hydrogen or a saturated or unsaturated, linear or branched, aliphatic radical optionally at least mono-substituted by hydroxy, fluorine, chlorine, bromide or trifluoromethyl,
with the proviso that $R^8$ and $R^9$ are not hydrogen at the same time, and if one of them, $R^8$ or $R^9$, is a saturated or unsaturated, linear or branched, $C_1$-$C_4$ aliphatic radical optionally at least mono-substituted by hydroxy, fluorine, chlorine, bromide or trifluoromethyl, the other one is a saturated or unsaturated, linear or branched, aliphatic radical with at least five carbon atoms optionally at least mono-substituted by hydroxy, fluorine, chlorine, bromide or trifluoromethyl, or $R^8$ and $R^9$ together with bridging nitrogen atom form a saturated or unsaturated, optionally at least mono-substituted heterocyclic ring, which may contain at least one additional heteroatom as a ring member and/or may be condensed with a saturated or unsaturated, optionally at least mono-substituted mono- or bicyclic cycloaliphatic ring system, which may optionally contain at least one heteroatom as a ring member, wherein each one of the substituents may be chosen from hydroxy, fluorine, chlorine, bromide, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, A represents a phenyl or napthyl ring optionally at least mono-substituted by fluorine, chlorine, bromine, linear or branched $C_1$-$C_6$ alkyl, linear or branched $C_1$-$C_6$ alkoxy, linear or branched $C_1$-$C_6$ alkylthio, trifluoromethyl radical, cyano radical or $-NR^{12}R^{13}$ radical, wherein $R^{12}$ and $R^{13}$, identical or different, represent hydrogen or a linear or branched $C_1$-$C_6$ alkyl; and
n is 0, 1, 2, 3 or 4;
optionally in form of one of its stereoisomersin any mixing ratio, or a salt thereof.

2. A compound according to claim 1, wherein $R^1$ represents a $-NR^8R^9$ radical or a saturated or unsaturated optionally at least mono-substituted 5- or 6-membered cycloaliphatic radical, which may optionally contain at least one heteroatom as a ring member and which may be condensed with a saturated or unsaturated, optionally at least mono-substituted mono- or bicyclic cycloaliphatic ring, which may optionally contain at least one heteroatom as a ring member, whereby the rings of the ring system are 5- or 6-membered, wherein each of the substituents may be chosen from hydroxyl, fluorine, chlorine, bromide, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl.

3. A compound according to claim 1, wherein $R^2$, $R^3$, $R^5$, $R^6$ and $R^7$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical, wherein each of the substituents may be chosen from hydroxy, fluorine, chlorine, bromide and trifluoromethyl.

4. A compound according to claim 1, wherein $R^4$ represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical, wherein each of the substituents may be chosen from hydroxy, fluorine, chlorine, bromide and trifluoromethyl.

5. A compound according to claim 1, wherein $R^8$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical, a linear or branched, optionally at least mono-substituted $C_2$-$C_{10}$ alkynyl radical, wherein each of the substituents may be chosen from hydroxy, fluorine, chlorine, bromide and trifluoromethyl, or $R^8$ and $R^9$ together with bridging nitrogen atom form a saturated or unsaturated, optionally at least mono-substituted 5- or 6-membered heterocyclic ring which may contain at least one additional heteroatom as a ring member and/or which may be condensed with a saturated or unsaturated, optionally at least mono-substituted mono- or bicyclic cycloaliphatic ring, which may optionally contain at least one heteroatom as a ring member, whereby the rings of the ring system are 5- 6- or 7-membered, wherein each one of the substituents may be chosen from hydroxy, fluorine, chlorine, bromide, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl.

6. A compound according to claim 5, wherein $R^8$ and $R^9$, identical or different, each represent hydrogen or a linear or branched $C_1$-$C_{10}$alkyl radical, or $R^8$ and $R^9$ together with the bridging nitrogen atom form a radical chosen from the group consisting of

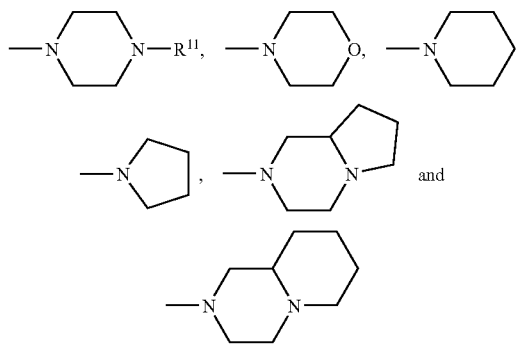

wherein $R^{11}$, if present, represents hydrogen, a linear or branched $C_1$-$C_6$ alkyl radical or a benzyl radical.

7. A compound according to claim 1, wherein A represents a radical chosen from

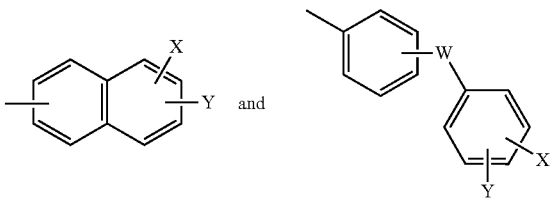

wherein X and Y independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl.

8. A sulfonamide compound of general formula (Ib),

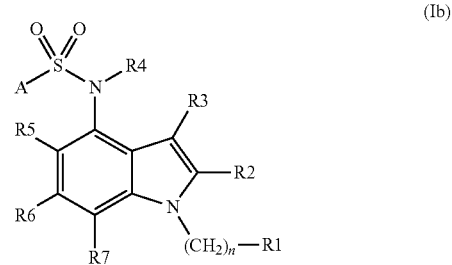

(Ib)

wherein $R^1$ represents a —$NR^8R^9$ radical, $R^2$, $R^3$, $R^5$, $R^6$ and $R^7$, identical or different, each represent hydrogen, halogen, nitro, alkoxy, cyano, a saturated or unsaturated, linear or branched, aliphatic radical optionally at least mono-substituted by hydroxy, fluorine, chlorine, bromide or trifluoromethyl, or a phenyl or a heteroaryl radical, $R^4$ is hydrogen or a saturated or unsaturated, linear or branched, aliphatic radical optionally at least mono-substituted by hydroxy, fluorine, chlorine, bromide or trifluoromethyl, $R^8$ and $R^9$, identical or different, each represent hydrogen or a saturated or unsaturated, linear or branched, $C_{1-4}$ aliphatic radical optionally at least mono-substituted by hydroxy, fluorine, chlorine, bromide or trifluoromethyl, A represents an optionally at least mono-substituted phenyl or naphthyl ring optionally at least mono-substituted by hydroxyl, halogen, linear or branched $C_1$-$C_6$ alkyl, linear or branched $C_1$-$C_6$ alkoxy, —O-phenyl, linear or branched $C_1$-$C_6$ perfluoroalkyl, linear or branched $C_1$-$C_6$ perfluoroalkoxy, 5- or 6-membered heteroaryl, or phenyl radical optionally at least mono-substituted by fluorine, chlorine, bromine, linear or branched $C_1$-$C_6$ alkyl, linear or branched $C_1$-$C_6$ alkoxy, linear or branched $C_1$-$C_6$ alkylthio, trifluoromethyl radical, cyano radical or —$NR^{12}R^{13}$ radical, wherein $R^{12}$ and $R^{13}$, identical or different, represent hydrogen or a linear or branched $C_1$-$C_6$ alkyl, and n is 0, 1, 2, 3 or 4;

optionally in form of one of its stereoisomers in any mixing ratio, or a salt thereof.

9. A compound according to claim 8, wherein $R^2$, $R^3$, $R^5$, $R^6$ and $R^7$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical, wherein each of the substituents may be chosen from hydroxy, fluorine, chlorine, bromide and trifluoromethyl.

10. A compound according to claim 8, wherein $R^4$ represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical, wherein each of the substituents may be chosen from hydroxy, fluorine, chlorine, bromide and trifluoromethyl.

11. A compound according toclaim 8, wherein $R^8$ and $R^9$, identical or different, each represent hydrogen or a linear or branched, $C_1$-$C_4$ alkyl radical optionally at least mono-substituted by hydroxy, fluorine, chlorine, bromide and trifluoromethyl.

12. A compound according to claim 8, wherein A represents A represents a radical chosen from

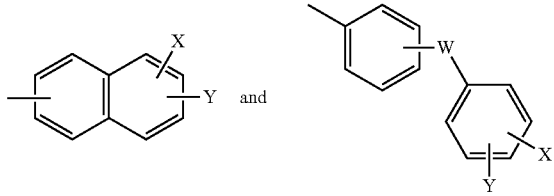

wherein X and Y independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl.

13. A compound according to claim 8 selected from the group consisting of

[2] N-[1-(2-dimethylaminoethyl)-1H-indole-4-yl]-naphtalene-2-sulfonamide,

[3] N-[1-(2-dimethylaminoethyl)-1H-indole-4-yl]-naphtalene-1-sulfonamide,

[4] N-[1-(2-dimethylaminoethyl)-1H-indole-4-yl]-4-phenylbenzenesulfonamide,

[5] N-[1-(2-dimethylaminoethyl)-1H-indole-4-yl]-2-(naphtalene-1-yl)-ethanesulfonamide,

[6] N-[1-(2-dimethylaminoethyl)-1H-indole-4-yl]-4-phenoxybenzenesulfonamide,

[7] N-[1-(2-dimethylaminoethyl)-1H-indole-4-yl]-3,5-dichlorobenzenesulfonamide and their corresponding salts.

14. A process for obtaining a sulfonamide of general formula (Ia) according to claim 1, wherein a compound of general formula (II), or one of its suitably protected derivatives,

wherein A has the meaning according to claim 1, and X is an acceptable leaving group, is reacted with at least one 4-aminoindole of general formula (III), or one of its suitably protected derivatives;

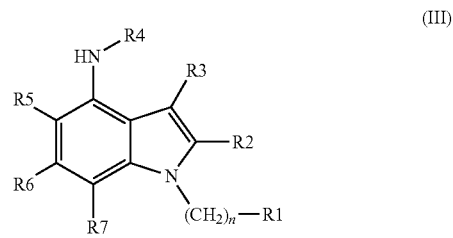

wherein $R^1$-$R^7$ and n have the meaning according to claim 1 to obtain the corresponding sulfonamide and optionally, from the latter, the protective groups may be removed.

15. A process for obtaining a sulfonamide of general formula (Ia) according to claim 1, wherein $R^1$-$R^3$, $R^5$-$R^7$, n and A have the meaning according to claim 1, and $R^4$ represents $C_1$-$C_6$ alkyl, the process comprising reacting at least one compound of general formula (Ia), wherein $R^1$-$R^3$, $R^5$-$R^7$, n and A have the meaning according to claim 1, and $R^4$ represents an hydrogen atom, with an alkyl halogenide or dialkyl sulfate.

16. A process for preparing salts of the compounds of general formula (Ia) according to claim 1, the process comprising reacting at least one compound of the general formula (Ia) with a mineral acid or organic acid in a suitable solvent.

17. A composition comprising least one compound according to claim 1 and one or more pharmacologically acceptable excipients.

18. A composition comprising at least one compound according to claim 8 and one or more pharmacologically acceptable excipients.

* * * * *